(12) United States Patent
Darnell

(10) Patent No.: US 6,340,301 B2
(45) Date of Patent: *Jan. 22, 2002

(54) DEVICE FOR HEATING THE TEETH AND USES THEREFOR

(76) Inventor: Daniel Henry Darnell, 508 Bango Ave., Hanceville, AL (US) 35077

( * ) Notice: Subject to any disclaimer, the term of this patent is extended or adjusted under 35 U.S.C. 154(b) by 0 days.

This patent is subject to a terminal disclaimer.

(21) Appl. No.: 09/791,529

(22) Filed: Feb. 23, 2001

Related U.S. Application Data

(63) Continuation of application No. 09/506,847, filed on Feb. 18, 2000, now Pat. No. 6,254,391, which is a continuation-in-part of application No. 09/247,124, filed on Feb. 8, 1999, now Pat. No. 6,102,705, which is a continuation-in-part of application No. 08/968,802, filed on Nov. 22, 1997, now abandoned.

(51) Int. Cl.[7] ............................................... A61C 15/00
(52) U.S. Cl. ......................................... 433/216; 433/32
(58) Field of Search .............................. 433/32, 34, 35, 433/37, 80, 2, 15, 216, 229; 607/108, 109, 113, 134, 96, 98, 99

(56) References Cited

U.S. PATENT DOCUMENTS

| | | | |
|---|---|---|---|
| 1,084,017 | A | 1/1914 | Lautenburg |
| 2,167,467 | A | 7/1939 | Sisson |
| 4,735,571 | A | 4/1988 | Salvo |
| 4,968,251 | A | 11/1990 | Darnell |
| 4,983,381 | A | 1/1991 | Torres Zaragoza |
| 4,990,089 | A | 2/1991 | Munro |
| RE34,196 | E | 3/1993 | Munro |
| 5,575,655 | A | 11/1996 | Darnell |
| 6,102,705 | A | 8/2000 | Darnell |

*Primary Examiner*—Ralph A. Lewis
(74) *Attorney, Agent, or Firm*—Lanier Ford Shaver & Payne, P.C.; Gerald M. Walsh; David L. Berdan

(57) ABSTRACT

There is disclosed a novel device for providing heat to dental and periodontal structures and a novel process for brightening teeth, together with a novel use of old known processes for brightening teeth. The novel device comprises a splint/stint or vacumformed dental tray, containing a heating element to be placed around the tooth or teeth to be brightened. The novel process for brightening/whitening teeth entails using the splint containing the heating element in conjunction with standard tooth whiteners with a brightening agent. The heating element is attached to a power source, preferably mobile and transportable, so that the process may be accelerated by the heating of the brightening agent, in accordance with the Q10 rule.

40 Claims, 3 Drawing Sheets

DEVICE FOR HEATING THE TEETH AND
USES THEREFOR

This is a continuation of U.S. patent application Ser. No. 09/506,847, filed Feb. 18, 2000, now U.S. Pat. No. 6,254, 391 which is a continuation-in-part of U.S. patent application Ser. No. 09/247,124, filed Feb. 8, 1999, issued as U.S. Pat. No. 6,102,705, which is a continuation-in-part of U.S. patent application Ser. No. 08/968,802 filed on Nov. 22, 1997, abandoned.

BACKGROUND OF THE INVENTION

1. Field of the Invention

This invention relates to an improved process and apparatus for brightening teeth, utilizing a heating element that activates a brightening agent, and more particularly to such a process that is user activated and controlled, within a short interval of time, thus decreasing the conventional time required for effective teeth whitening.

2. Technical Background

The importance of cosmetically attractive, whitened or brightened, teeth in today's society cannot seriously be questioned. During the past ten years, there has been a virtual explosion of supposed new and improved processes for the simplification and efficacy of teeth whitening and brightening. However, each such process has had several drawbacks creating a negative impact on the user, including high costs of the new treatments, repeated visits to the dentist/cosmetician for repeated treatments, difficulty of use, length of time to achieve the desired results, and need for professional help.

The prior art has known many devices and methods for externally treating a tooth or teeth of a patient. The most primitive method of externally treating a tooth involved the direct application of an active agent to the tooth of the patient. Examples of the external treatment of a tooth include the direct application of active agents such as fluoride, tooth whiteners, antibiotics, antihistamines and topical anesthetics.

Although the external treatment of a tooth by the direct application of an active agent has achieved some success, several problems exist with this method. First, the direct application of an active agent is generally inefficient since the active agent can be applied to the surface of the tooth for only a relatively short period of time with only modest results. The relatively short period of time of application is determined by the length of time the active agent remains on the tooth of the patient. The length of time the active agent remains on the tooth of the patient is generally determined by the viscosity of the active agent and the ability of the active agent to remain on the tooth as well as the ability of the patient to remain immobile during the treatment.

In an effort to overcome these problems, some in the prior art have increased the concentration of the active agent in an effort to produce satisfactory results within the limited period of time permitted by the direct application of the active agent. Unfortunately, the increase in concentration of the active agent produces undesirable side effects for the patient.

Many other prior art treatment processes have also involved the direct application of a physical process to the external surface of a tooth to brighten same, involving, for example, the use of bonding to mask previously existing stains on the tooth, crowns or porcelain veneers physically attached to the tooth to in effect hide the stains, or application of high physical heat through the past use of a modified soldering iron, a heat lamp or today's equivalent, a laser. However, all of these applications involved the direct need for a professional doctor and/or dentist chair time and the resulting associated costs. The user has had little control over the process being applied to his teeth, and had to frequently revisit his doctor/dentist for follow-up application and treatments.

The remaining treatment processes have tried to give the user some sort of control over the bleaching and whitening process, but usually at the expense of time and efficiency, and with varying results. For example, others in the prior art have utilized a plastic splint or stint molded to overlay the teeth of the patient in an effort to retain a tooth whitening agent in contact with the teeth of the patient over an extended period of time. Such a method is set forth in an article entitled "Nightguard Vital Bleaching" which has been published in *Quintessence International*, Volume 20, March, 1989. In this method, a stint is molded to fit the entire upper or lower teeth of the patient and to seal with the gingiva of the patient. The active agent is introduced into the stint and the stint is inserted upon the teeth of the patient to retain the active agent in close contact with the teeth of the patient.

Although the use of a plastic stint allowed the active agent to remain in contact with the teeth for an extended period of time, the use of the plastic stint had certain disadvantages. First, since the plastic stint was molded to intimately fit with the entire upper or lower teeth of the patient, the stint was uncomfortable due to the tightness of the fit with the teeth. Second, the stint sealed with the gingiva of the patient, making the stint incapable of fitting with a single tooth or just several teeth. Third, the stint had to be cut back adjacent to the gingival margin to prevent undesired deterioration of the gingiva due to the intimate contact of the stint with the gingiva during the treatment process. Forth, the intimate fit of the stint with the entire upper or lower teeth of the patient prevented ingress and egress of oxygen to the internal regions of the stint. Fifth, the intimate fit of the stint with the entire upper or lower teeth of the patient made the stint difficult to remove in some instances. Sixth, notwithstanding the intimate region of the stint with the entire upper or lower teeth of the patient, the active agent within the internal region of the stint would over time migrate from the stint, thus reducing the effectiveness of the active agent upon the teeth.

The liquid splints/stints utilized by the Munro patent, U.S. Pat. No. RE 34,196, the disclosure of which is hereby incorporated by reference, constituted a great advance in the art at the time and did permit some freedom of use by the user. However, the splints still required several hours of use of the liquid splint per day for many days to achieve the desired brightening effects, and were uncomfortable to some due to their tightness over the teeth. There was also a problem involving the retention of the brightening agent on the treated teeth. Several inventions followed which attempted to resolve the problems of the whitening agent being swallowed, dissolved/weakened by saliva, or leaking out of the splint onto the gums/gingiva or labia. Several other new processes were introduced which addressed the retention of whitening agent through the additions of a retaining material/reservoir (U.S. Pat. No. 4,968,251) and plurality of indentations/baffles to prevent the loss of the whitening agent (U.S. Pat. No. 5,575,655). However, these later inventions/processes did not sufficiently address the time and efficiency issues of the user, though they did allow the user more freedom in his control over the bleaching process.

In the effort to reduce the time needed for the bleaching process, some in the prior art have tried to increase the concentration and/or the viscosity of the whitening agent (see, e.g. Fischer U.S. Pat. No. 5,098,303), thereby hoping to speed up the brightening process while lowering the time the user had to use the splint of Munro or later modified and improved versions of same. However, the increased concentration and/or viscosity of the brightening agent—frequently a peroxide derivative—resulted in an accompanying increase in deleterious side effects for the user. To avoid tissue damage from the increased concentration of the brightening agent, the user had to frequently shorten his exposure to same with intervening periods of no exposure—with the result that the overall bleaching time (time to achieve whitened/brightened teeth) has remained more or less similar.

There have been additional techniques and devices developed over the years in an effort to improve the methods for brightening or whitening teeth. One such effort was the application of heat to dental and/or periodontal structures and the whitening agents, such as peroxides, being applied thereto. It is widely known in the art that heat activates peroxide solutions, increasing their effectiveness as whitening agents. Under the "Q10 Rule," it is well known in the art that an increase of 10° C. in temperature of whitening agents/solutions-such as peroxides and peroxide derivatives—doubles the speed of the whitening action/process. In other words, the time to achieve whitening results is effectively halved. Thus, whitening time can be reduced by 50% by application of a sufficient supra-body heat temperature to the whitening agent.

For this reason, the application of heat to dental and/or periodontal structures and the whitening agents has long been a desired treatment parameter, but the lack of control of the amount of heat or the difficulty associated with the delivery of a therapeutic quantity of heat for sufficient time to be useful along with the degree of discomfort to the patient has limited the use of heat in various dental/periodontal treatments. For example, in an article entitled "Bleaching Tetracycline-Stained Vital Teeth" published in Oral Surg., March 1970, a method was introduced to bleach certain stained teeth by the application of 30% hydrogen peroxide (Super oxol) to individual teeth warmed or heated by a modified soldering iron (bleaching tool) to the individual's limit for pain (pain threshold), for a period of 30 minutes over 8 treatments, spanning a two-month period. All treatments had to be conducted in the dentist's office, with follow-up visits to maintain bleaching monthly thereafter. The inventors noted that this bleaching technique would be contra indicated for any tooth bearing a silicate/resin restoration. Interestingly, the pulp temperature remained constant and unchanged during treatment.

With the advent of Munro, the slight advantages offered by the prior art heating source method—and its progeny— were overcome, as the tray technology of Munro and its progeny achieved equivalent teeth whitening results by longer exposure times to peroxide activated by body heat. The art tried to counter the Munro progeny trays with better sources of heat and peroxides to counter the relative ease of the Munro trays with better whitening results. Photo flood lights, hot irons (soldering irons), hot water baths and lasers have all been recorded in the art as methods of activating, and heating, peroxide compounds for teeth whitening procedures. With the exception of some of the hot water bath techniques, all of these heating methods must be practiced by a dentist or other medical professional in the office due to the cumbersome and non-portable natures of these heat sources; these methods are not at home techniques. As a result, office procedures are costly on a per hour basis, especially when many hours of treatment may be necessary over an extended number of days. Thus, in an effort to maximize results within short time periods, therefore decreasing "chair time" at the dental office, high concentrations of whitening solutions (peroxide compounds) have been required in addition to uncomfortably high levels of heat.

In a typical tray-type whitening method utilizing Munro and its progeny, a tray is loaded with carbamide peroxide, or other similar bleaching/whitening agent, and placed over the teeth to be whitened. The tray is then left in contact with the teeth for a prescribed period of time, during which time some whitening or bleaching of the tooth/teeth occurs. Repeated applications are necessary as whitening of the tooth/teeth occurs in small increments over a period of several weeks. The degree of whitening is dependent, in part, on the amount and concentration of the whitening solution and the time in which said solution remains in contact with the teeth, as well as the susceptibility of the tooth to this whitening procedure.

The only remaining variable is the temperature under which the bleaching/whitening action takes place. Currently, in all tray-type whitening methods, the bleaching/whitening takes place at body temperature (inside of the mouth), though some methods perform a preliminary step of warming the whitening agent (by immersing same into a bowl of warm water) to obtain a temporary body-like or greater temperature before the placement of the whitening agent within the tray. However, no current tray-type method utilizes sustained supra-body heat temperature, and the constant maintenance of same, on the whitening agent during the whitening/bleaching process. This problem is further exemplified and exacerbated due to the user's/patient's mouth being open during use of the tray; the inhale/exhale process brings room temperature air over the teeth constantly. Thus, simple breathing thereby lowers the temperature of the whitening agent and thus lowers the reaction speed, thereby increasing the total time needed for the user to obtain whitened teeth.

Therefore, there is a need in the art for a simplified and less costly process of tooth brightening that the user can do, either at home or during a single trip or two to the dentist/doctor's office, without the serious side effects associated with an increase in the concentration of the whitening agent. A further need exists in the art for a simplified process of tooth brightening associated with a maintenance system for the now whitened/brightened teeth, said process being within the total control and ability of the user.

SUMMARY OF THE INVENTION

It is an object of the present invention to provide an improved method and apparatus for treating a tooth or teeth with an active agent which produces results which are superior to the results heretofore known to the art. This is accomplished by use of a dental device comprising a splint, a heating element attached to the splint, and a means for increasing the temperature of the heating element. In another embodiment of the present invention, an active whitening agent is placed in the splint to assist in whitening the teeth.

Another object of the present invention is to provide an improved method and apparatus for treating a tooth or teeth with an active agent wherein said active agent is retained in a custom-fitted splint and catalyzed by a heating element used in conjunction with said custom-fitted splint.

In multiple embodiments of the present invention, the means for increasing the temperature of the heating element include a battery connection, with a standard rechargeable battery, or some other external power source.

The foregoing has outlined some, not all, of the more pertinent objects of the present invention. Said objects should not be construed to be illustrative of all pertinent features and applications of the present invention, but merely illustrative of some of the more pertinent features and applications of the invention. Many other beneficial results can be obtained through the use of the disclosed invention—whether same is applied in a different manner or otherwise modified within the scope of this disclosure. Therefore, a more full understanding of the present invention may be obtained by referring to the drawings, the summary of the invention and the detailed description describing the preferred embodiment of same, with the scope of the invention being defined by the claims and illustrated by said attached drawings.

DETAILED DESCRIPTION OF THE INVENTION

Figure 1:
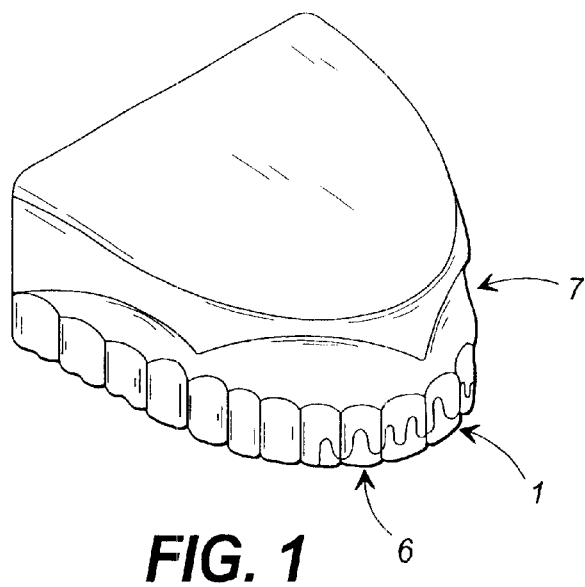
FIG. 1 is a depiction of the heating element wire bent and formed over a mold of a set of upper teeth in a manner as to cover a maximum surface per tooth to provide even heat displacement.

It has been discovered that the bleaching/whitening agents currently being utilized within the liquid splints/trays of Munro and progeny in the prior art can be further activated by the constant application of heat on said bleaching/whitening agent by means of a heating element within said liquid splint/tray, and adjacent to the whitening agent, thereby activating and accelerating the bleaching/whitening process of stained or otherwise discolored teeth, while remaining in the control of the user. The present invention provides a method and process for placing a heated element within a liquid splint or tray, with said heated element connected to a power source, such as a typical D-cell battery, thereby providing an increase in the temperature of the bleaching/whitening agent above normal body temperature (98.6° F.) with a subsequential and consequential increase in the bleaching/whitening reaction, pursuant to the Q10 Rule. This permits the whitening procedure to be accomplished in a shorter period of time than current conventional tray whitening techniques allow. A further benefit of the invention is that, due to the increased reaction rate of the whitening agent, a user with sensitive teeth/gums can still undergo the whitening process in the same amount of time as the current conventional techniques, but with a lesser concentration of whitening agent, thereby lowering the risk of pain, discomfort, and damage a user faces with higher concentrations of said whitening agent. Together, the invention would thus achieve greater whitening efficiency and in a faster time, retain control of the procedure with the user, and provide results at a fraction of the costs of professional whitening.

Specifically, this invention pertains to the technique of mouth guard, night guard or tray-type teeth whitening whereby a custom or non-custom fitted splint is used in conjunction with a heated element to increase the effectiveness of a bleaching agent contained within said splint to whiten teeth. The heated splint is offered to the art as a simple, economical and novel method of applying heat to a single tooth or plurality of teeth and whitening agent within a patient's/user's mouth. This heat application is utilized to increase efficiency and uniformity of the bleaching or whitening process over all state-of-the-art modalities. This method allows precise control over the amount of heat delivered to the tooth structures, as heat is focused via this heated tray method within a specific area and has minimal, if any, affect on surrounding structures.

Due to the predictable heat level produced by the heated tray for sustained time periods (0-unlimited time, dependent on power sources), and also due to the simple and portable nature of its design, lower concentrations of whitening solution can be used to obtain similar results to said prior art heat source methods used in office procedures. Lower temperatures can also be employed to obtain similar results because the time of treatment can be easily extended without consuming expensive office treatment time; the patient/user can utilize the technique at home.

Because lower concentrations of whitening solution can be utilized, there will be a lower incidence of side effects related to the concentration and/or components of the whitening solution. Furthermore, due to the lower levels of heat which can be used, there will also be less side effects related to the high levels of heat previously used in the art. It has been shown in many studies that teeth are resilient to moderate levels of heat and are not permanently adversely effected by application of said moderate levels of heat, up to approximately 160° F.

Therefore, the heated tray technique will allow the use of the most conservative components of a teeth whitening regimen while still obtaining the greatest possible whitening effect in the shortest period of time. The heated tray technique and invention as disclosed herein constitutes the new state-of-the-art of teeth whitening, since all the variables of time, whitening agent concentration, and temperature can be controlled by the user at home. Any of the custom trays derived from Munro (U.S. Pat. No. RE 34,196), its progeny, Darnell (U.S. Pat. No. 4,968,251) and Darnell (U.S. Pat. No. 5,575,655) may be utilized in connection with the heated tray technique, along with the over the counter non-custom trays and the "boil and bite" semi-custom trays. Specifically, the invention utilizes all the embodiments referred to in Munro U.S. Pat. No. RE 34,196, Darnell U.S. Pat. No. 4,968,251, and Darnell U.S. Pat. No. 5,575,655 and all such embodiments in said patents are hereby incorporated by reference into this application.

The heated tray whitening method now allows the patient total control over the whitening process. The patient can control the level of heat to the desired level of comfort via a potentiometer (voltage regulator or rheostat) or by simply activating and deactivating the battery/power source. The patient also controls the concentration of the whitening solution according to each individual's sensitivity to the concentration of the whitening agent. Furthermore, and perhaps most importantly to the user, the patient can control the time regimen for utilizing the heated tray whitening method that fits their own schedule. For example, a patient can use the heated tray one hour per day or only twenty minutes per day. Due to this level of control over the whitening method, the patients can whiten their teeth until they are satisfied that their teeth are as white as each particular patient desires.

Figure 2:
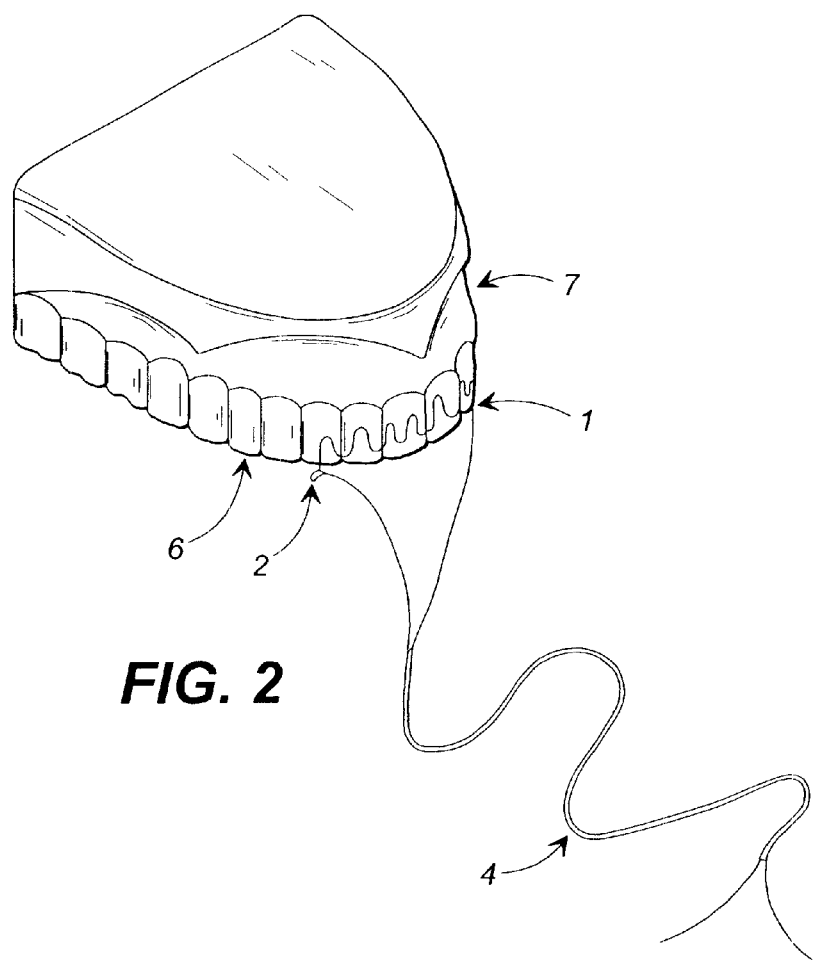
FIG. 2 is a depiction of the heating element wire attached via solder to an insulated power supply wire.
Figures 3, 4:
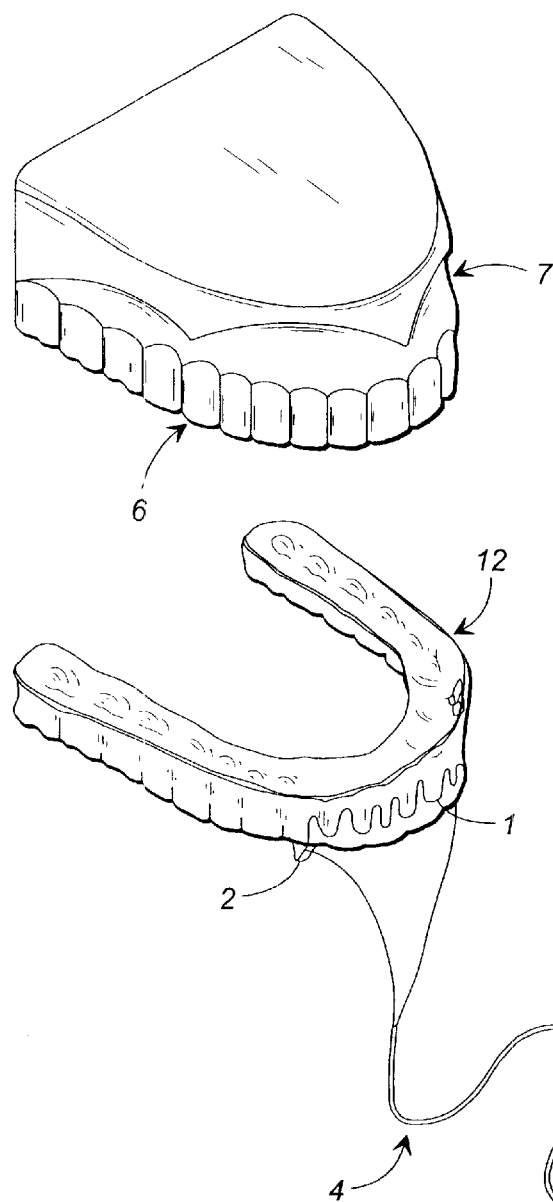
FIG. 3 is a depiction of a mold of a set of upper teeth and the splint therefore constructed following standard dental procedures. The heating element wire is encased in the splint and the insulated power supply wire protrudes from the splint and is attached to a power source.
FIG. 4 is a depiction of the heating element wire encased in a heat dispensing pad bent and formed over a mold of a set of upper teeth.
Figure 5:
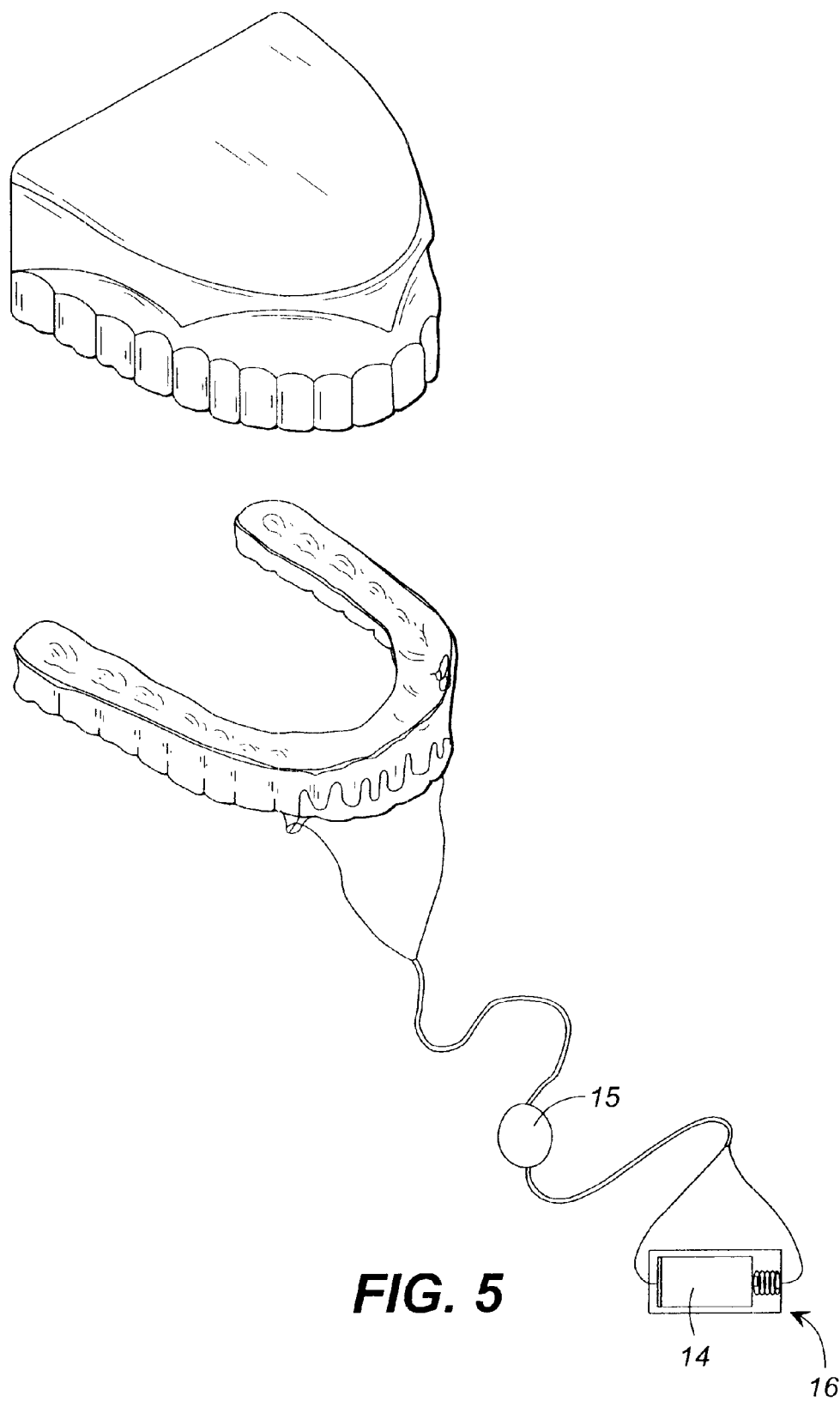
FIG. 5 is a depiction of the splint with the heating element wire encased in the splint and the insulated supply wire protruding from the splint. The insulated power supply wire is connected to a potentiometer or other voltage regulator which is connected to the power source, a battery.

FIG. 1 illustrates the heating element wire 1 formed over a mold of a set of upper teeth. The heating element wire 1 preferably consists of a 3–4 inch length of nickel-chromium alloy (or other similarly electrically conductive) wire bent or formed in such a manner as to cover a maximum width per tooth 6 to provide even heat displacement over a greater width than the thickness of the wire 1 itself. Other materials may be used for the heating element, such as, for example, polyimide/FEP, etched foil, mica, ceramics, carbon-based conducting materials, or a combination thereof An insulated power supply wire 4 is attached via solder 2 or clip, or some other electromechanical attaching means, to each end of said heating element wire 1, as depicted in FIG. 2. There are many possible and potential configurations for the heating element wire 1. The nichrome, or other similarly conductive, wire 1 is preferably 27 gauge with no cover or padding and approximately 3–5 inches in length. A longer length of heating element wire 1 may require a higher gauge. For example, seven inches of heating element wire 1 would preferably be about 35 gauge, while a lesser length of heating element wire 1 would preferably use a lower gauge. For example, 2.5 inches of heating element wire 1 may be 25 gauge, in order to maintain similar therapeutic temperatures of approximately 110° using identical power sources 8 (i.e. a 1.5 volt D-cell battery). The heating element wire 1 may be encased in a heat dispensing pad 9 such as cotton felt or acrylic, or some other electrically insulated/inert material, as depicted in FIG. 4. A power supply wire 4 is again attached to the two ends of the heating element via wire 1 solder or other means. This resulting unit, i.e., the heating element wire 1 and the solder 2 or other attaching means is the portion that will be bonded, molded or otherwise attached into the whitening tray. The heating element wire 1 cannot be allowed to form a cross-circuit, i.e. cross itself, since if uninsulated, the wire 1 could in effect "short out," thus changing the effective length of the heating element wire 1, and the resultant temperature/heat delivered to the tooth/teeth surface(s) 6. The other end insulated power supply wire is connected to the power supply, as depicted in FIG. 3.

In one embodiment, the heating element wire 1 is bonded within the facial wall 13 of a "custom" tray 12, i.e., the inner aspect of the tray or splint which contacts the front surface of the teeth. In this manner, the heating element provides heat directly to the front surface of the teeth and the whitening agent is heated at the front surface of the teeth. The "custom" tray 12 is fabricated by means common to the art; herein the "custom" tray 12 may be fabricated by molding the tray with the heating element wire 1 over a stone (or plaster) model 5 of the specific user's/patient's teeth to be whitened utilizing a dental vacumform machine. The stone or plaster model 5 may be formed from an alginate impression of the patient's/user's upper or lower arch of teeth, with the impression then being used to fabricate the stone or plaster model 5. The stone model 5 is fabricated and trimmed through the palatal/lingual surface until the maxillary and mandibular models have a horseshoe appearance. A die spacer or some other suitable material is placed on the surface (buccal and/or lingual) of the teeth to be preferentially treated. The heating element wire 1 would actually be placed on, and attached to the stone model 5, said attachment being preferentially accomplished through small drops of a superglue being applied to the desired location on the maxillary and/or mandibular model, and the heating element wire 1 then glued/tacked to said location. Selected tray material, typically 0.040 EVA material or a polycarbonate composition, is then heated in the vacumform unit, while the patient's/user's model 5 with attached/affixed heating element wire 1 is placed on the vacumform stage or some other similar flat work space. The heated tray material, after being heated in the vacumform machine to a molten temperature, is then pulled down and forced over the model 5 and the heating element wire 1. The sealing of the heating element wire 1, save for the protrusions of the two power supply wires 4, within the tray 12 by the vacumform tray material also prevents any excess leakage of the whitening agent from the incisal section of the tray at the point the power supply wire 4 protrudes from the tray (i.e. where the heating element wire 1 connects to, and with, the power source or power source supply wire 4). The nichrome wire portion of the heating element wire 1 is generally sealed, away from the teeth surface, by the vacumformed tray material, though it may be only partially sealed, and has a resultant location on the inner aspect of the tray 12, which contacts the front surface of the teeth. The tray 12 is then trimmed in the standard manner, according to the prior art, slightly to the tooth side and away from the gingival tissue 7 side. As is known in the prior art, the tray 12 should not overlie gingival tissue 7, i.e. no tray material should touch the gingivae at the neck areas of the teeth when the tray is in use with the peroxide agent/solutions, so as to reduce possible injury or irritation to the gingival tissue 7.

The heating element wire 1 may also be bonded into a generic or universal tray, such as a commercially available over-the-counter tray or splint as described above, i.e., the heating element is located within the inner aspect of the splint which contacts the front surface of the teeth. This unit is not "custom-formed" for each particular user, or "patient," and thus would be suitable for "over-the-counter" applications for at home teeth whitening by the user. By way of example, and not by limitation, a standard "thin" football or other sport mouthpiece/mouth guard is utilized and the heating element wire 1 is either made or molded into the inner aspect of said mouth guard, which contacts the front surface of the teeth. If the heating element wire 1 is desired to be encased in said mouth guard, such could be performed using the techniques outlined above, i.e., forming the heating element wire 1, attaching the power supply wire 4 by solder 2 or other means, and placing same into the generic or universal mold before the tray material is deposited. As an alternative to encasing the heating element wire 1 in the mouthpiece, the heating element wire 1 can be molded and attached to the tray, after the tray material is deposited into the mold. The increments on the mouth guard can then be trimmed off to avoid contact with the gingival tissue 7, such that the level of the whitening solution/bleaching agent 11 is visible. The whitening treatment would then proceed by activating the tray with a power source 8, ideally in this incarnation a portable battery, such as a D or C-cell battery.

The non-custom tray or splint with heating element contained therein can also be heat-fitted, such as a known art technique of a mouth guard which is boiled or heated until it becomes soft, and the user then forms an impression of his teeth by biting into the new soft mouth guard and letting same cool for a specified period of time. The non-custom tray would then be "semi-custom," as the user could buy a conventional mouth guard, then mold it to fit only his/her teeth in the usual "boil and bite" mouth guard method.

Due to the lesser periods of time needed for the user to obtain whitened teeth by this procedure, some of the "comfort" normally required by the user for use of a bleaching/whitening tray can be sacrificed. Less time in the non-custom but heated tray would mean less time being uncomfortable, but with the same or similar results as those currently obtained by custom-tray techniques that do not utilize a heating element. The user who could withstand a temporary sacrifice in comfort would save money over the more costly conventional custom-tray techniques which utilize dental impressions, stone or plastic models of same, etc. Accordingly, for some users, the non-custom heated tray can be a viable and cost-effective alternative to more costly techniques.

The non-custom or "over-the-counter" heated tray may be best used with the lower concentrations of carbamide peroxide, or similar bleaching agents/whitening solutions 11, due to less potential side effects, i.e. burned gingival tissue 7 caused by lesser control over the peroxide solutions in the non-custom trays as compared to higher levels of control over said solutions when a user utilizes custom trays. The lower level or concentration of the peroxide solutions are also recommended in this technique due to the sole control by the user over the process; the process is generally unsupervised by a dental or professional doctor. Due to lower concentrations of the whitening solution and lower levels of heat this method could be effective but take more time than the dentist supervised custom tray incarnation described above.

The heating element wire 1 may also be bonded to either the custom tray or generic tray in such a manner so that the felt (or cotton or acrylic) surface of the heat dispensing pad 9 of the heating element wire 1 is in direct contact with the teeth 6, or may instead be bonded or attached in such a manner that the heating element wire 1 and heat dispensing pad 9 are entirely bonded and enclosed by the tray material. The layers of the tray material would in effect "sandwich" the heating element and would be in direct contact with the front surface of the teeth. In either method, the two power supply wires 4 connected to the heating element wire 1 can protrude through or over the tray material. The power supply wire 4 can be routed in any convenient manner as long as the power source is connected to the heating element wire 1.

In another embodiment, the device can be made by placing a spacer on the surface of a tooth mold, forming a splint over the mold, removing the formed splint and spacer from the mold, removing the spacer from the splint, placing a heating element within the splint, and connecting the heating element to a power source to increase the temperature of the heating element.

The steps of a) placing a heating element on the surface of the mold, b) connecting the power supply wires to each end of heating element, and then c) forming the splint are equivalent to the steps of a) attaching the power supply wires to each end of the heating element b) placing the heating element on the surface of the mold, and then c) forming the splint, which is also equivalent to the steps of a) placing a heating element on the surface of the mold, b) forming the splint, and then c) attaching the power supply wires to each end of the heating element.

Regardless of the incarnation selected, the heating element wire 1 is then activated by a power supply 8 by means of a power supply wire 4 between said power supply : and heating element wire 1, as depicted in FIG. 3. The power supply 8 used to activate the heating element wire 1 could be one or more D-cell alkaline batteries. Almost any size battery 14 will enable the heating element wire 1 to obtain the desired temperature and include D-cell, C-cell sizes, as well as multiples of A and AA-cell size batteries. The battery 14, which in one incarnation may be encased in a battery case 16, may be replaced after each treatment, depending on the size of the battery 14 initially used and the length of treatment. A typical D-size battery will provide approximately 4–5 hours worth of treatment time, or approximately 3–5 individual treatments. The power supply 8 may have a variable potentiometer 15, or voltage regulator/rheostat device, to allow the patient, or doctor/dentist if treated within an office, to vary the temperature of the heated tray and utilize/achieve a more comfortable temperature setting consistent with each patient's desire. It may also alternatively utilize a cap on the battery casing 16 which upon closure onto the battery case 16 would activate the heating element wire 1. A "dead man" switch may also be incorporated into an incarnation of the invention, such that the power supply 8 to the heating element wire 1 is turned off should the user let go of said switch, such as by falling asleep. The switch would be attached in one incarnation of the invention to the battery casing 16. The temperature range of the heating element wire 1, activated once the battery 14 is installed, or in other incarnations turned on via the cap on the battery casing 16 or via a dead man's switch will be between 90–160° F., preferably 100–125° F., more preferably 105–110° F.

The heated tray may also be fabricated wherein both the heating element wire and the power supply 8 are located within the heated tray. In this incarnation of the invention, a small 1.5 volt camera battery, for example, is attached by means of a clip, solders or other electrical attaching means known to the art to the heating element wire 1 prior to the sealing of the heating element wire 1 and the battery 14 by the vacumform tray material. The internal power source 8, such as a camera or watch battery, would be attached to the stone model 5 by means similar to the attachment of the heating element wire 1 to said stone model 5, or by other attaching means. A "dead-man's" switch, to enable or disconnect the electrical circuit/heating element wire 1 as discussed below, is attached to the outside (labial) surface of the heated tray. Alternatively, the battery 14 could be placed inside yet another (second) tray which would be placed over the first tray, so-called double vacumforming, which would seal both the battery 14 and the heating element wire 1 within the tray material so that the danger of a patient/user swallowing the battery 14 would be drastically lessened. The expected life of such a power source 8 within said heated tray incarnation should extend beyond a 2-hour treatment time for most normal cases. For serious cases, multiple heated trays of this incarnation would have to be fabricated and later utilized by the patient/user. The battery in this self-contained tray can most conveniently be located in a "handle" attached to the tray which protrudes form the patient's mouth, and said battery can be, preferably, rechargeable.

Once the power supply 8 is activated, standard 54–4%, preferably 10–22% carbamide peroxide solution, peroxide formulations including peroxide gel solution, fluoride composition or other similar whitening/bleaching agent 11, is loaded into the tray. The tray is then placed over the teeth 6 to be whitened for a prescribed period of time or "dosage." The tray is left in place and the whitening agent/solution is replaced at necessary intervals for normal tray use. If trays such as those disclosed in U.S. Pat. Nos. 4,968,251 or 5,575,655 are utilized, there may be no need to add additional whitening solution 11, due to the indentations, reservoirs and baffles within said trays as per said inventions.

As with conventional tray-type tooth whitening, the frequency of use and the duration of such use is dependent on how white the patient desires his teeth, how amenable the teeth are to the whitening procedure, and the degree and type of stain present. Depending on these factors, it would not be unlikely that certain patients may need to repeat applications using this process for several times a day, an hour per treatment, over a one or two week period. For such serious cases however, the bleaching/whitening tray-techniques utilizing the heated tray will still be faster than conventional ha tray-type whitening techniques and cheaper than the conventional laser/light/heat bleaching techniques, pursuant to the application of the Q10 Rule.

The heated tray can be applied by the user for selected times, for example varying from 10 minutes up to 2 hours or more at steady and consistent heat levels, or applied with steady and consistent heat levels for alternating intervals of heat and non-heat (i.e. cooling) periods, such as 5 minutes heat on alternating with 5 minutes heat off for a period of one or two hours. The tray can also be applied using rising or changing heat levels up to a maximum tolerance or comfort level, depending on each such user, for example a 15 minute to 2 hour time frame, or alternatively for intervals of heat on and increasing for a specified time frame, followed by a cooling off interval. Such uses can be directed by the doctor/dentist, or by the individual desires of the user. These uses have been accomplished through utilization of a "C" or "D" cell batteries (one or more per heating element, one heating element per heated tray), a 4.5" 27 gauge nichrome wire and a "dead man's" switch (said switch being held to activate the circuit/heating element; loss of hold on the switch deactivates said circuit/heating element).

Since each and every individual user will have a different tolerance for the amount of heat supplied, and the concentration of the whitening agent, a visit to a dentist/doctor to evaluate each patient's/user's sensitivities to both temperature and the concentration of the whitening agent/solution is recommended. Variances in temperature to meet each patient's/user's need can be met through the use of the variable potentiometer/voltage regulator/rheostat mentioned above. Sensitivities to the strength (concentration) of the whitening agent/solution used can be overcome by using less concentrated agents which, given the invention's decrease in whitening time through the application of constant measured heat to the teeth, may still permit the subject teeth to be whitened within the same period of time with no loss of efficiency over the prior art. Alternatively, various agents can be applied to the gums (gingival tissues) to decrease exposure to the whitening agents. Some of the more common agents include the petrolatum compounds, such as petroleum jelly or Vaseline, which can be applied either to the gum tissues prior to the loading and placement of the tray within the mouth and/or applied to the exposed gum tissues after the heated tray is placed over the teeth to be treated. Other agents to protect the gingival tissues include "paint on rubber dams" and equivalents, which can likewise be applied in a manner similar to the application of the petrolatum compounds.

In a preferred embodiment of the invention, the heating element wire 1 is composed of a 27 gauge nichrome wire of 4" length, which is looped and attached within the vacum-formed custom fitted tray 12, and connected to a battery case containing two C-cell batteries regulated by a 25 ohm variable wound rheostat, connected to a 24 inch length of 24 gauge wire, soldered to the nichrome wire. The nichrome wire is vacuformed and encased in 0.040" thickness EVA dental tray material. The unit can be controlled by an on/off switch within the rheostat. In this embodiment, batteries 14 produce a sustained temperature of approximately 110° F. for the duration of the bleaching/whitening application process. The vacumformed tray, as noted above, can contain indentations for excess bleaching/whitening agent—in this case 16% carbamide peroxide, pursuant to incorporated U.S. Pat. No. 5,575,655.

The amount of heat generated is dependent upon the length of nichrome wire, the gauge of nichrome wire, the power level applied, and the thickness and composition of said heat dispensing pad, if such a pad is used. The following examples outline the amount of heat generated by various combinations of wire length, wire gauge, and battery type.

EXAMPLE 1

| 4" Length | 27 Gauge Nichrome | Thermometer Insulated Wire Wrapped | New D-Cell Battery |
|---|---|---|---|
| Time | | Element Temperature (° F.) | |
| 0 | | 77.5 | |
| 30 sec | | 82.4 | |
| 1 min | | 93.9 | |
| 1 min 30 sec | | 104.0 | |
| 2 min | | 112.2 | |
| 2 min 30 sec | | 117.7 | |
| 3 min | | 122.0 | |
| 3 min 30 sec | | 125.0 | |
| 4 min | | 127.0 | |
| 4 min 30 sec | | 128.1 | |
| 5 min | | 128.5 | |
| 5 min 30 sec | | 129.5 | |
| 6 min | | 129.2 | |
| 6 min 30 sec | | 128.3 | |
| 7 min | | 127.9 | |
| 7 min 30 sec | | 127.1 | |
| 8 min | | 126.5 | |
| 8 min 30 sec | | 126.1 | |
| 9 min | | 126.1 | |
| 9 min 30 sec | | 126.0 | |
| 10 min | | 125.3 | |
| 10 min 30 sec | | 123.8 | |
| 11 min | | 124.1 | |
| 12 min | | 122.3 | |
| 13 min | | 121.6 | |
| 14 min | | 122.6 | |
| 15 min | | 122.9 | |
| 16 min | | 124.0 | |
| 17 min | | 124.2 | |
| 18 min | | 125.2 | |
| 19 min | | 124.5 | |
| 20 min | | 124.3 | |

EXAMPLE 2

| 5" Length | 27 Gauge Nichrome | Wrapped/Insulated | New D-Cell Battery |
|---|---|---|---|
| Time | | Element Temperature (° F.) | |
| 0 | | 78.2 | |
| 30 sec | | 79.4 | |
| 1 min | | 85.1 | |
| 1 min 30 sec | | 90.1 | |
| 2 min | | 94.5 | |
| 2 min 30 sec | | 98.6 | |
| 3 min | | 103.3 | |
| 3 min 30 sec | | 103.8 | |
| 4 min | | 105.3 | |
| 4 min 30 sec | | 106.1 | |
| 5 min | | 107.1 | |
| 5 min 30 sec | | 107.4 | |
| 6 min | | 107.8 | |
| 6 min 30 sec | | 108.0 | |
| 7 min | | 108.2 | |
| 7 min 30 sec | | 108.3 | |
| 8 min | | 108.3 | |

-continued

| 5" Length | 27 Gauge Nichrome | Wrapped/Insulated | New D-Cell Battery |
|---|---|---|---|
| Time | | Element Temperature (° F.) | |
| 8 min 30 sec | | 108.2 | |
| 9 min | | 107.9 | |
| 9 min 30 sec | | 107.8 | |
| 10 min | | 108.1 | |
| 11 min | | 108.5 | |
| 12 min | | 108.2 | |
| 13 min | | 107.6 | |
| 14 min | | 107.5 | |
| 15 min | | 107.3 | |
| 16 min | | 107.0 | |
| 17 min | | 106.9 | |
| 18 min | | 106.9 | |
| 19 min | | 106.7 | |
| 20 min | | 106.5 | |
| 21 min | | 106.7 | |
| 22 min | | 106.8 | |
| 23 min | | 106.1 | |
| 24 min | | 106.0 | |
| 25 min | | 106.0 | |
| 26 min | | 106.1 | |
| 27 min | | 105.6 | |
| 28 min | | 105.4 | |
| 29 min | | 105.4 | |
| 30 min | | 105.3 | |
| 31 min | | 105.1 | |
| 32 min | | 105.1 | |
| 33 min | | 105.2 | |
| 34 min | | 105.0 | |
| 35 min | | 105.1 | |
| 36 min | | 104.9 | |
| 37 min | | 105.0 | |
| 38 min | | 105.0 | |
| 39 min | | 105.4 | |
| 40 min | | 105.8 | |
| 41 min | | 105.2 | |
| 42 min | | 105.2 | |
| 43 min | | 105.0 | |
| 44 min | | 104.7 | |
| 45 min | | 104.2 | |
| 46 min | | 104.0 | |
| 47 min | | 103.9 | |
| 48 min | | 103.6 | |
| 49 min | | 103.8 | |
| 50 min | | 103.6 | |
| 60 min | | 104.2 | |
| 65 min | | 103.5 | |
| 70 min | | 103.2 | |
| 75 min | | 102.6 | |
| 80 min | | 102.2 | |
| 85 min | | 102.1 | |
| 90 min | | 102.2 | |
| 95 min | | 101.3 | |
| 100 min | | 102.4 | |
| 105 min | | 102.2 | |

EXAMPLE 3

| 3 1/8" Length | 27 Gauge Nichrome | Wrapped* | New D-Cell Battery |
|---|---|---|---|
| Time | | Element Temperature (° F.) | |
| 0 sec | | 73.4 | |
| 30 sec | | 82.0 | |
| 1 min | | 97.0 | |
| 1 min 30 sec | | 190.2 | |
| 2 min | | 118.0 | |
| 2 min 30 sec | | 122.3 | |
| 3 min | | 121.1 | |

-continued

| 3 1/8" Length | 27 Gauge Nichrome | Wrapped* | New D-Cell Battery |
|---|---|---|---|
| Time | | Element Temperature (° F.) | |
| 3 min 30 sec | | 128.3 | |
| 4 min | | 130.6 | |
| 4 min 30 sec | | 131.0 | |
| 5 min | | 129.6 | |
| 5 min 30 sec | | 128.9 | |
| 6 min | | 128.1 | |
| 6 min 30 sec | | 130.1 | |
| 7 min | | 130.3 | |
| 7 min 30 sec | | 131.4 | |
| 8 min | | 130.6 | |
| 8 min 30 sec | | 129.4 | |
| 9 min | | 129.4 | |
| 9 min 30 sec | | 129.0 | |
| 10 min | | 128.4 | |
| 11 min | | 126.7 | |
| 12 min | | 128.0 | |
| 13 min | | 125.7 | |
| 14 min | | 128.5 | |
| 15 min | | 129.6 | |
| 16 min | | 130.0 | |
| 17 min | | 130.1 | |
| 18 min | | 130.3 | |
| 19 min | | 130.6 | |
| 20 min | | 129.2 | |

*Wrapped around sensor with tape insulation to avoid "shorting" the Nichrome

EXAMPLE 4

| 3" Length | 27 Gauge Nichrome | Wrapped** | 2 D-Cell Batteries |
|---|---|---|---|
| Time | | Element Temperature (° F.) | |
| 30 sec | | 125.0 | |
| 45 sec | | 138.0 | |
| 1 min | | 151.3 | |
| 1 min 30 sec | | 169.2 | |
| 2 min | | 186.0 | |
| 2 min 30 sec | | 191.0 | |

**Nichrome wire wrapped around sensor of thermometer

2 D-cell batteries quickly heated past 191° F. which is too hot for this invention's use. Use of a variable resistor—such as a rheostat—would increase the circuit's resistance to the power source and thereby lower the temperature of the heating element.

EXAMPLE 5

| 4" Length | | 27 Gauge Nichrome | |
|---|---|---|---|
| Battery Type | | Time | Wire Temperature (° F.) |
| Duracel P x 28A  6 volt (Photo/Electronic) Miniature Battery | | 1 min | 83.0 |
| | | 2 min | 83.8 |
| | | 3 min | 84.4 |
| | | 4 min | 87.8 |
| | | 5 min | 87.8 |
| Catalog No.: 23-266A Radio Shack  6 volt | | 0 sec | 84.0 |
| | | 30 sec | 89.4 |

-continued

| | 4" Length | | 27 Gauge Nichrome |
|---|---|---|---|
| Lithium | 160 milli amps | 1 min | 90.4 |
| | | 2 min | 91.3 |
| | | 3 min | 91.0 |
| | | 4 min | 89.2 |
| | | 5 min | 88.2 |
| 1.5 v Size N | 0 sec | 82.0 | |
| Radio Shack | | 30 sec | 98.5 |
| 2/23-023 | 340 milli amps | 1 min | 113.2 |
| | | 1 min 30 sec | 120.2 |
| | | 2 min | 123.5 |
| | | 2 min 30 sec | 126.3 |
| | | 3 min | 124.7 |
| | | 3 min 30 sec | 125.6 |
| | | 4 min | 125.6 |
| | | 4 min 30 sec | 126.5 |
| | | 5 min | 126.7 |
| | | 5 min 30 sec | 128.8 |
| | | 6 min | 126.5 |
| | | 6 min 30 sec | 125.6 |
| | | 7 min | 124.0 |
| | | 7 min 30 sec | 124.0 |
| | | 8 min | 123.0 |
| | | 8 min 30 sec | 123.1 |
| | | 9 min | 122.6 |
| | | 9 min 30 sec | 122.0 |
| | | 10 min | 121.6 |
| | | 11 min | 119.9 |
| | | 12 min | 117.0 |
| | | 13 min | 113.6 |
| | | 14 min | 113.0 |
| | | 15 min | 113.9 |
| | | 16 min | 111.7 |
| | | 20 min | 113.5 |
| | | 25 min | 112.3 |
| | | 30 min | 88.2 0.05 (milli amps) |

| Gauge Nichrome | Length (Inches) | Power | Solution Temperature ° F. in the Tray |
|---|---|---|---|
| 27 ga. | 3.0 | 1.5 v D-cell battery | ~112.6 |
| 27 ga. | 3.5 | 1.5 v D-cell battery | ~110.1 |
| 27 ga. | 4.0 | 1.5 v D-cell battery | ~108.2 |
| 27 ga. | 4.5 | 1.5 v D-cell Battery | ~106.6 |

These temperatures are for solution temperature in the tray at room temperature on table top.

EXAMPLE 7

Wire temperature using variable rheostat with 1 D-cell 1.5 v battery Variable resistor used in this test allows 0–94 MA 4" 27 gauge Wire 1.5 v D-cell Eveready Classic 71.4 room temperature for 30 seconds 12 MA—no temperature change

| Time | Element Temperature (° F.) |
|---|---|
| 1 min | 72.0 |
| 1 min 30 sec | 75.0 |
| 2 min | 78.2 |
| 2 min 30 sec | 81.8 |
| 3 min | 84.0 |
| 3 min 30 sec | 85.3 |
| 4 min | 86.9 |
| 4 min 30 sec | 87.8 |
| 5 min | 88.2 |
| 5 min 30 sec | 88.5 |
| 6 min | 89.1 |
| 6 min 30 sec | 89.8 |
| 7 min | 90.5 |
| 7 min 30 sec | 90.6 |
| 8 min | 90.9 |
| 8 min 30 sec | 91.0 |
| 9 min | 91.6 |
| 9 min 30 sec | 91.6 |
| 10 min | 91.7 |
| 11 min | 92.0 |
| 12 min | 91.0 |
| 13 min | 91.0 |
| 14 min | 91.3 |
| 15 min | 91.0 |
| 16 min | 91.2 |
| 17 min | 91.6 |
| 18 min | 91.8 |
| 19 min | 91.9 |
| 20 min | 92.1 |
| 30 min | 92.6 |
| 45 min | 93.3 |
| 60 min | 93.0 |

Analysis of the above results, and application to the present invention, depends upon the understanding of the Q10 Rule.

The Q10 Rule states: "For every 10° C. (18° F.) in temperature, the reaction rate doubles."

Since:
Our heated tray temperature=110° F. (for example)
Body temperature=98.6° F. Actual mouth temperature=<90° F.

Using this data, which is conservative, the heated tray produces an approximate 20° F. increase in actual bleaching temperature over the regular method.

Actual tooth temperature is less than bleaching surface temperature due to the fact that enamel and dentin are excellent insulators. Hence, pulpal temperatures are only minimally effected. Surface temperatures of 124° F. have been used for years and are well known to the art for teeth bleaching. Pulpal trauma has proven not to be a problem with even this high level of heat. Anesthetic is never used in any heat bleaching technique in order that the individual patient may control the bleaching process (i.e., the level of heat being applied by the heated tray) and prevent any discomfort (by varying or discontinuing treatment). All teeth are different and have differing sensitivities to heat, therefore, tray temperature should be adjusted on a personal basis. A pulpal temperature rise is maintained below 8° F. at all times. Whitening concentration is similarly adjusted on a personal basis with the availability of 10%, 16%, 20% and 44% carbamide peroxide solutions.

Also, current state of the art treatment regimens vary with personal preferences, such as one hour per day for 21 days or 18 hours per day regimens. The current state of the art allows a selection of whitening agents viscosities and concentrations as well as time regimens. The current state of the art allows no control of the susceptibility of any particular tooth to the whitening process. However, experience proves that most teeth are susceptible to teeth whitening procedures—illustrated by the fact that 95% of general dentists dispense take home teeth whitening kits.

The heated tray allows an individual desiring whiter teeth to control the last remaining variable, temperature, proven in the art to increase efficacy. Heat is proven to activate peroxide based whitening solutions, causing them to whiten teeth faster than the same solution would whiten teeth without the addition of heat.

The very fact that teeth whitening occurs with peroxide based solutions retained by a dental tray as well as it does without heat activation is a factor of the current long time periods of treatment required for successful, retained results. This is why the heated tray has such value. It can increase the whitening rate from 2 to 4 times the state of the art. Therefore, the patient can obtain the same whitening in half of the time or less! The physics of reaction rates required that any tooth that would whiten by 4 vita shades in 10 hours of treatment, using the state of the art method, would whiten 4 vita shades in 5 hours or less of treatment using the heating tray.

EXAMPLE 8

Clinical results show 3–4 vita shade changes observed after one hour of treatment. A vita shade change of $A_4$ to $A_1$ was observed following one hour of treatment with 20% carbamide peroxide in viscous solution using 4.5" length of nichrome wire as a heating element prepared in a custom tray powered by a fresh 1.5 v D-cell extra strength battery. Tray temperatures remained well within the comport level of the patient. Effective teeth whitening was visibly appreciated by the patient immediately upon removing the heating tray. As with all teeth whitening treatments, repeated exposures to the whitening solution increase the permanence of the whitening effect.

EXAMPLE 9

Another clinical test demonstrated excellent results of a vita shade change of $B_3$ to a $B_1$ was observed using 4 separate one hour treatments over a two day period. The heated tray was constructed with a heating element wire consisting of a 4.0 inch length of 27 gauge nichrome wire, powered by a fresh 1.5 v D-cell extra strength battery. A viscous solution of 16% carbamide peroxide was placed into the heated tray, at the beginning of treatment and again after 30 minutes of treatment. (The energy from the heated tray activates the carbamide peroxide whitening solution and therefore exhausts its whitening effect two to four times faster than regular tray-type whitening. Accordingly, the whitening solution must be replenished more frequently). The whitening procedure was followed for one hour, at which time the tray was removed and the teeth were brushed with water to remove the viscous whitening solution that remained on the teeth (teeth were visibly whiter). After a one hour rest period, the heated tray whitening was begun again with a fresh 1.5 v D-cell extra strength battery and a viscous solution of 16% carbamide peroxide. The solution was replenished after 30 minutes of treatment. After the hour was complete, the tray was removed and the teeth brushed with water to remove retained carbamide peroxide. At this point, the teeth were observed to be a vita shade $B_1$ in effect, the whitest shade for these particular teeth. No whiter tooth shade was available on the guide for comparison.

The following day treatment with the heated tray was commenced again. The same heated tray was used with a fresh same type of 1.5 v D-cell battery. It was noted that some reversion to original shade was observed—to approximately a vita shade $B_2$. The treated teeth were still visibly whiter than the untreated teeth of the lower area. Treatment was identical to the previous day. After the first one hour session (replenished solution after 30 minutes) the teeth were completely white, vita shade $B_1$. The teeth were brushed with water and a period of one hour elapsed at which point treatment began with fresh solution and a fresh battery. The whitening solution was replenished after 30 minutes. The whitening procedure ended after one hour and teeth were determined to have whitened as much as was possible. The teeth were brushed with water to remove excess carbamide peroxide from all surfaces. The patient observed that it felt like the teeth were still bleaching even though the treatment was finished and the tray was removed. Thus it appears that part of the success of this technique is that with the heating of the solution, penetration of the tooth structure by the whitening solution is increased, therefore, the whitening effect still occurs for a short time even after treatment has been discontinued. This would help explain the results that are obtained in such a short period of time.

EXAMPLE 10

A commercially available battery on/off variable resistor was obtained.

This device used two AA size (1.5 v each) 1.5 batteries and was found to deliver 0 MA at the off position. The device delivered 74 MA at the lowest setting and 208 MA at the highest setting.

The following wire temperature results were obtained utilizing nichrome wire of 27 gauge 4" length with a room temperature of 66.8° F.

| Time | Element Temperature (° F.) |
| --- | --- |
| On Low | |
| 30 sec | 74.6 |
| 1 min | 79.1 |
| 1 min 30 sec | 83.3 |
| 2 min | 86.1 |
| 2 min 30 sec | 87.9 |
| 3 min | 89.2 |
| 3 min 30 sec | 89.6 |
| 4 min | 89.8 |
| 4 min 30 sec | 89.8 |
| Dialed to High | |
| 30 sec | 94.1 |
| 1 min | 104.8 |
| 1 min 30 sec | 112.4 |
| 2 min | 115.5 |
| 2 min 30 sec | 117.1 |
| 3 min | 113.4 |
| 3 min 30 sec | 114.5 |
| 4 min | 117.2 |
| 4 min 30 sec | 119.8 |
| 5 min | 121.3 |
| 5 min 30 sec | 121.8 |
| 6 min | 121.8 |
| 6 min 30 sec | 121.2 |
| 7 min | 120.2 |
| 8 min | 119.3 |
| 9 min | 117.9 |
| 10 min | 114.8 |
| 11 min | 112.5 |
| 12 min | 111.2 |
| 13 min | 110.0 |
| 14 min | 109.0 |
| 15 min | 107.9 |
| 20 min | 106.9 |

Teeth whitening procedures with the heated tray showed dramatic results after the first treatment. This is very encouraging to patients who undergo teeth whitening treatment. The fact that they see quick results will generally motivate them to continue the procedure. It encourages them to repeat the treatment enough to obtain and maintain the color teeth they desire.

The heated tray technology allows the individual greater control of the teeth whitening process. Not only can the patient control the concentration of the whitening solution, as in the prior art, but they can also control the time to a greater degree, by controlling the temperature of the whitening process. This allows for better and faster results than have ever been possible; using moderate concentrations of whitening solutions, with moderate levels of heat, over greater time periods, than was possible sitting in a dentist chair. The heated tray will quickly become the state of the art when used either by itself as the whole whitening procedure or in alternation with standard non-heated tray type tooth whitening, whereby an individual may use the heated tray at home and a conventional tray between heated tray treatments. In any case, heated tray technology will revolutionize teeth whitening.

The heated tray/splint of the present invention has several other uses in addition to whitening of the teeth. Because heat is applied directly to the front surface of the teeth by the present invention relatively selectively, a significant amount of heat can be applied to the teeth without heating other structures of the mouth or making the user uncomfortable. This feature allows the present invention to be useful in the treatment of mouth odor, dentin sensitivity, tooth demineralization, tooth decay, and periodontal disease.

Bad breath is a major concern to the general population and treatment is a source of an important profit industry worldwide. This condition affects about 50 to 60 percent of the population. The most common cause of bad breath is elevated levels of volatile sulfur compounds, primarily hydrogen sulfide and methylmercaptan, arising from the metabolism of protein by anerobic gram-negative bacteria retained in periodontal pockets. These compounds, besides producing odor, are highly toxic to tissues and may play a role in the pathogenesis of inflammatory conditions such as periodontitis. Heat applied to the teeth by the present invention can help destroy bacteria, especially when used with other treatments added to the tray, such as, for example, hydrogen peroxide, carbamide peroxide, fluoride solutions, Peridex®, conventional mouthwash solutions, or a combination thereof.

Treatment of dentin hypersensitivity is of increasing importance in the daily practice of dentistry. Dentin hypersensitivity affects nearly 40 million Americans at one time or another. Dentin hypersensitivity is caused by a change in fluid flow in the dentinal tubules, which excites nerve endings located in the dentinal tubules and at the pulp-dentine border area. Traumatic oral hygiene procedures, excessive use of acid containing dietary fluids, and certain dental treatments have been important in the occurrence of dentine hypersensitivity. Several desensitizing treatments applied to the teeth are known to reduce pain associated with dentin hypersensitivity, such as, for example, solutions of potassium nitrate, fluoride, strontium chloride, sodium citrate, gutaraldehyde, or combinations thereof Treating the teeth with the tray/splint of the present invention will substantially improve the efficacy of these agents, individually, or in combiantion, by increasing the rate and extent of uptake and penetration of these agents into dentinal tubules, protecting the nerve endings. These agents can be added to the tray while heating the teeth so that the heat and desensitizing treatment can be applied simultaneously.

The heated tray/splint of the present invention may be used to prevent and treat tooth decay and periodontal disease. Heating the teeth with the tray/splint can destroy bacteria such as $S.$ $mutans$ and gram negative bacteria that cause tooth decay and periodontal disease. The tray/splint can also be used in combination with antibacterial agents, such as, for example, Peridek® and Perioguard®.

Demineralization and remineralization control the progression and reversal of carious lesions in teeth, respectively. Tooth demineralization and remineralization can be described as naturally occurring dynamic processes in the oral enviornment. Ions, such as calcium and phosphate are dissolved from the tooth mineral into saliva and are precipitated back from saliva into the teeth. Under normal physiologic conditions, the rates of demineralization and remineralization are equivalent, resulting in no net loss of tooth mineral. It is only when the balance between these two processes is disturbed that destruction of mineralized tissue occurs. A localized decrease in pH, such as that produced by bacterial plaque, can change the dynamics in favor of demineralization and result in a carious lesion. More generalized changes in pH, such as those caused by frequent intake of acidic foods or beverages, can also result in the generalize demineralization associated with tooth erosion or root surface sensitivity. Although many conditions associated with loss of tooth mineral have multiple causes, the basic mechanism is demineralization. The formation of a cavity will be prevented if the average amount of demineralization that occurs is equal to or exceeded by the average amount of remineralization.

Saliva provides a natural source of calcium and phosphate ions for remineralization. However, in the absence of fluoride, saliva is not a very effective remineralizing medium. Increasing the fluoride content of saliva has been correlated with increased rates of remineralization and decreased caries incidence. It has been shown that even trace concentrations of fluoride ions are effective in promoting calcium hydroxyapatite (tooth mineral) formation from supersaturated solutions of calcium and phosphate. For this reason, fluoride is added to toothpastes, mouthrinses, and drinking water as an anticaries agent. One of fluoride's primary modes of action is to increase the uptake of calcium and phosphate ions—the building blocks of tooth mineral—from saliva into demineralized lesions in tooth enamel to promote remineralization. A likely reason why fluoride is not more effective in preventing decay is that the remineralization process is limited by the availability of calcium and phosphate ions in saliva. If supplemental concentrations of calcium and phosphate ions could be supplied to saliva without insolubilizing the fluoride, the effectiveness of fluoride could be increased.

The tray/splint of the present invention overcomes this problem by providing heat to the teeth and to solutions within the tray/splint containing fluoride, calcium, and phosphate. The heat applied by the tray/splint to the front surface of the tooth increases the solubility and concentration of calcium, phosphate, and fluoride ions in the solution and further increases the rate and extent of penetration and uptake of these ions into the tooth, thereby providing an improved remineralization procedure. In this manner, the present invention can be used to prevent, arrest, or reverse tooth decay in carious areas.

From the foregoing description of the preferred embodiments of the invention it will be apparent that many modifications may be made therein. It should be understood, however, that these embodiments are intended merely as an exemplification of the invention and that the invention is not limited thereto. It should be understood, therefore, that it is intended that in the appended claims to cover all such modifications in the true spirit and scope of the invention.

I claim:

1. A device for heating the teeth, comprising:
   a) a dental splint having an inner aspect for contacting the front surface of the teeth directly, said splint constructed to cover the entire structure of the teeth but not the gingival tissue;

b) a heating element within said inner aspect of said splint adapted to contact the front surface of the teeth directly and to heat the front surface of the teeth directly;

c) a means for increasing the temperature of said heating element;

d) said splint having a reservoir to hold a fluid treatment solution in contact with the teeth but not in contact with the gingival tissue; and e) said splint constructed to fit entirely within the mouth and to cover the entire structure of the teeth.

2. The device of claim 1 wherein the heating element reaches a temperature between 90–160° F.

3. The device of claim 2 wherein said means for increasing the temperature of said heating element comprises a battery powered electrical circuit connected to said heating element.

4. The device of claim 3 wherein said means for increasing the temperature of said heating element is comprised of:

a) a power source;

b) a first electrically conductive wire having a first and second end; and c) a second electrically conductive wire having a first and second end, wherein the first end of both the first and second wire are connected to said heating element and the second end of both the first and second wire are connected to the power source such that an electrical circuit is created that causes the heating element to increase in temperature.

5. The device of claim 4 wherein said power source comprises one or more batteries.

6. The device of claim 5 wherein the heating element is comprised of a nickel-chromium alloy and wherein said heating element reaches a temperature between 90–160° F.

7. The device of claim 6 wherein said heating element is comprised of a nickel-chromium alloy, polyamide/FEP, etched foil, mica, ceramics, carbon-based conducting materials, or a combination thereof.

8. The device of claim 7 wherein said means for increasing the temperature of said heating element is embedded within the material forming the splint.

9. The device of claim 8 wherein said heating element is embedded within the material forming the splint.

10. The device of claim 9 wherein said heating element, within said inner aspect of said splint, is encased in a heat dispensing pad, bonded and enclosed by said splint.

11. The device of claim 10 wherein said splint is custom fitted to the teeth of a user.

12. The device of claim 11 wherein said splint is a semi-custom tray fitted by heat fitting by a user in need thereof.

13. The device of claim 12 further comprising a means for regulating the voltage provided by the power source to the electrical circuit.

14. The device of claim 5 wherein said battery is one or more C-cell batteries.

15. The device according to claim 14 wherein said fluid treatment solution contains peroxide, carbamide peroxide, fluoride, conventional mouthwash solutions, or a combination thereof to reduce mouth odor.

16. The device according to claim 14 wherein said fluid treatment solution contains a whitening agent to whiten the teeth.

17. The device according to claim 14 wherein said fluid treatment solution contains potassium nitrate, fluoride, strontium chloride, sodium citrate, glutaraldehyde, or combinations thereof to reduce dentin sensitivity.

18. The device according to claim 14 wherein said fluid treatment solution contains calcium, phosphate, and fluoride to prevent demineralization and to remineralize the teeth.

19. The device according to claim 14 wherein said fluid treatment solution contains one or more antibacterial agents to prevent and treat tooth decay and periodontal disease.

20. A method of treating teeth, comprising the steps of:

a) providing a splint constructed to cover the entire structure of the teeth but not the gingival tissue, said splint having an inner aspect for contacting the front surface of the teeth directly, and having a heating element within said inner aspect to contact the teeth directly and to heat the front surface of the teeth directly;

b) dispensing a fluid treatment solution into said splint, said splint having a reservoir to hold said fluid treatment solution in contact with the teeth but not in contact with the gingival tissue;

c) placing said splint entirely within the mouth;

d) placing said splint over the entire tooth or plurality of teeth to be treated such that the fluid treatment solution comes in contact with the tooth or plurality of teeth but not in contact with the gingival tissue; and e) providing heat directly to the teeth by increasing the temperature of the heating element contained therein with a power source so that the fluid treatment solution is heated at the front surface of the teeth.

21. The method of claim 20 wherein the heating element reaches a temperature between 90–160° F.

22. The method claim 21 wherein said power source for said heating element comprises an electrical circuit connected to said heating element.

23. The method of claim 22 wherein said power source for increasing the temperature of said heating element is comprised of:

a) one or more batteries;

b) a first electrically conductive wire having a first and second end; and c) a second electrically conductive wire having a first and second end, wherein the first end of both the first and second wire are connected to said heating element and the second end of both the first and second wire are connected to the power source such that an electrical circuit is created that causes the heating element to increase in temperature.

24. The method of claim 23 wherein the heating element is comprised of a nickel-chromium alloy and wherein said heating element reaches a temperature between 90–160° F.

25. The method of claim 24 wherein said heating element is comprised of a nickel-chromium alloy, polyamide/FEP, etched foil, mica, ceramics, carbon-based conducting materials, or a combination thereof.

26. The method of claim 25 wherein said power source for said heating element is embedded within the material forming the splint.

27. The method of claim 26 wherein said heating element is embedded within the material forming the splint.

28. The method of claim 27 wherein said heating element, within said splint, is encased in a heat dispensing pad, bonded and enclosed by said splint.

29. The method of claim 28 wherein said splint is custom fitted.

30. The method of claim 28 wherein said splint is a semi-custom tray fitted by heat fitting by a user in need thereof.

31. The method of claim 20 wherein a means for regulating the voltage provided by the power source to the electrical circuit is connected within the electrical circuit.

32. The method of claim 20 wherein the fluid treatment solution comprises a carbamide peroxide solution for whitening the teeth.

33. The method of claim 20 wherein the fluid treatment solution comprises a compound selected from the group consisting of carbamide peroxide, peroxide formulations, and fluoride for whitening the teeth.

34. The method of claim 32 wherein the fluid treatment composition consists essentially of from 5% to 44% carbamide peroxide.

35. The method of claim 20 wherein said fluid treatment solution contains peroxide, carbamide peroxide, fluoride, conventional mouthwash solutions, or a combination thereof to reduce mouth odor.

36. The method according to claim 20 wherein said fluid treatment solution contains potassium nitrate, fluoride, strontium chloride, sodium citrate, glutaraldehyde, or combinations thereof to reduce dentin sensitivity.

37. The method according to claim 20 wherein said fluid treatment solution contains calcium, phosphate, and fluoride to prevent demineralization and to remineralize the teeth.

38. The method according to claim 20 wherein said fluid treatment solution contains one or more antibacterial agents to prevent and treat tooth decay and periodontal disease.

39. The method according to claim 20 wherein no fluid treatment solution is used in said splint to heat the teeth to treat mouth odor.

40. The method according to claim 20 wherein the treatment of the teeth with said splint is entirely within the control and ability of a user in need of treatment of the teeth.

* * * * *